United States Patent
Kim et al.

(10) Patent No.: US 6,506,904 B1
(45) Date of Patent: Jan. 14, 2003

(54) METHOD OF PREPARING N,N'-DISUBSTITUTED-3,3'-DITHIODIPROPIONAMIDE AND METHOD OF PREPARING SUBSTITUTED 3-ISOTHIAZOLONE BY USING THE SAME

(75) Inventors: Seung-Hwan Kim, Suwon (KR); Jeong-Ho Park, Suwon (KR); Jin-Man Kim, Suwon (KR); Soon-Jong Hahn, Seoul (KR); Ki-Seong Choi, Anyang (KR); Myung-Ho Cho, Suwon (KR)

(73) Assignee: SK Chemicals Co., Ltd., Kyungki-do (KR)

( * ) Notice: Subject to any disclaimer, the term of this patent is extended or adjusted under 35 U.S.C. 154(b) by 0 days.

(21) Appl. No.: 10/152,118

(22) Filed: May 21, 2002

Related U.S. Application Data

(62) Division of application No. 09/937,747, filed as application No. PCT/KR99/00163 on Apr. 3, 1999.

(51) Int. Cl.$^7$ .............................. C07D 275/03
(52) U.S. Cl. .................. 548/213; 564/134; 564/154
(58) Field of Search ......................... 548/213

(56) References Cited

U.S. PATENT DOCUMENTS

| | | | | |
|---|---|---|---|---|
| 3,849,430 A | * | 11/1974 | Lewis et al. ............... | 260/302 |
| 4,868,310 A | * | 9/1989 | Chang ......................... | 548/213 |
| 5,024,659 A | * | 6/1991 | Sjostrom ..................... | 604/110 |
| 5,210,266 A | * | 5/1993 | Mimura et al. ............. | 558/254 |
| 5,453,507 A | * | 9/1995 | Hahn et al. ................. | 548/213 |
| 5,552,423 A | * | 9/1996 | Kakimizu et al ........... | 514/372 |
| 5,552,433 A | * | 9/1996 | Kakimizu et al. .......... | 514/372 |
| 5,663,436 A | * | 9/1997 | Kakimizu et al. .......... | 564/154 |
| 6,376,680 B1 | * | 4/2002 | Kim et al. .................. | 548/213 |

FOREIGN PATENT DOCUMENTS

| | | | |
|---|---|---|---|
| EP | 0437351 | * | 7/1991 |
| EP | 0648757 | * | 4/1995 |

\* cited by examiner

Primary Examiner—Shailendra Kumar
(74) Attorney, Agent, or Firm—Baker Botts L.L.P.

(57) ABSTRACT

A method of preparing N,N-disubstituted 3,3'-dithiodipropionamide of formula (2) is provided. In the method, 3-mercaptopropi-onamide of formula (4) reacts with an aqueous solution of amine to prepare N-substituted-3-mercaptopropionamide of formula (3) and

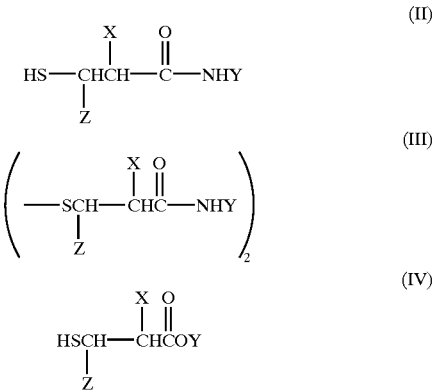

N-substituted-3-mercaptopropionamide reacts with an aqueous solution of hydrogen peroxide. In addition, a method of preparing substituted 3-isothiazolone is provided. In the method, the produced N,N-disubstituted-3,3'-dithiodipropionamide reacts with a halogenating agent, wherein X and Z are same or different and each selected from the group consisting of hydrogen or a lower alkyl group; Y is selected from the group consisting of hydrogen, an alkyl group of 1 to 18 carbon atoms, a cycloalkyl group of up to 10 carbon atoms, an aralkyl group of up to 10 carbon atoms, an alkyl group of up to 10 carbon atoms, a halogen-, lower alkyl- or lower alkoxy-substituted aryl group, cyano alkyl group, a carboalkoxyalkyl group, a haloalkyl group, an alkoxyalkyl group, an aryloxyalkyl group of up to 12 carbon atoms, an aralkoxyalkyl group of up to 12 carbon atoms, a dialkylaminoalkyl group, an alkylacyl group of up to 8 carbon atoms, a lower alkylsulfonyl group, an arylsulfonyl group of up to 10 carbon atoms, a cyano group and a carbamoyl group.

3 Claims, No Drawings

METHOD OF PREPARING N,N'-DISUBSTITUTED-3,3'-DITHIODIPROPIONAMIDE AND METHOD OF PREPARING SUBSTITUTED 3-ISOTHIAZOLONE BY USING THE SAME

This application is a divisional application Ser. No. 09/937,747, filed Sep. 28, 2001, which is a 371 of PCT/KR99/00/63, filed Apr. 3, 1999.

BACKGROUND OF THE INVENTION (a) Field of the Invention

The present invention relates to a method of preparing substituted 3-isothiazolone and, more particularly, to a method of preparing N,N'-disubistituted-3,3'-dithiodipropionamide and a method of preparing substituted 3-isothiazolone by using the same as a intermediate.

(b) Description of the Related Art

The substituted 3-isothiazolone of the formula 1 which synthesized by Crow et al., is widely used for disinfectants, biocides or microbiocides in paints, cosmetics or plastics.

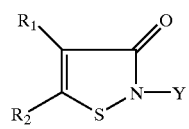

[Formula 1]

wherein Y is selected from the group consisting of hydrogen, an alkyl group of 1 to 18 carbon atoms, a cycloalkyl group of up to 10 carbon atoms, an aralkyl group of up to 10 carbon atoms, an aryl group of up to 10 carbon atoms, a halogen-, lower alkyl-, or lower alkoxy-substituted aryl group, a cyanoalkyl group, a carboalkoxyalkyl group, a haloalkyl group, an alkoxyalkyl group, an aryloxyalkyl group of up to 12 carbon atoms, an aralkoxyalkyl group of up to 12 carbon atoms, a dialkylaminoalkyl group, an alkylacyl group of up to 8 carbon atoms, a lower alkylsulfonyl group, an arylsulfonyl group of up to 10 carbon atoms, a cyano group and a carbarnoyl group;

$R_1$ and $R_2$ are same or different and each selected from the group consisting of hydrogen, halogen and a lower alkyl group.

U.S. Pat. No. 3,849,430 discloses a method of preparing substituted 3-isothiazolones. In the method, N,N'-disubstituted-3,3-dithiodipropionamide or N-substituted-3-mercaptopropionamide reacts with a halogenating agent, resulting in the cyclization of the amides. The N,N'-disubstituted-3,3'-dithiodipropionamide is prepared by reacting 3,3'-dithiodipropionic acid with amine in the form of gaseous atmosphere as the following reaction 1.

[Reaction 1]

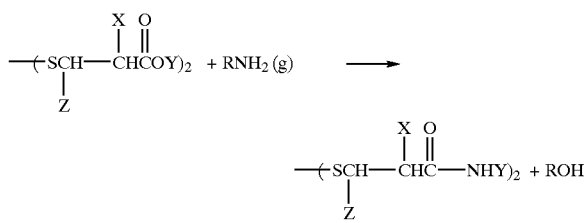

wherein Y is as defined above, X and Z are same or different and each selected from the group consisting of hydrogen and a lower alky group, R is selected from the group consisting of hydrogen, an alkyl group, a phenyl group, a cyano group, a sulfonyl group and a aminocarbonyl group.

The method can produces stable N,N'-disubstituted-3,3'-dithiodipropionamide with high yield. However, the produced N,N-disubstituted-3,3'-dithiodipropionamide has low purity and the reaction should be performed for a long time, i.e. 48 hours or more than. Furthermore, as the method uses amine in the form of gaseous atmosphere, the safety and environmental problems may occur.

N-substituted-3-mercaptopropionamide is prepared by reacting 3-mercaptopropionic acid. Prepared as described above, with alcohol to form 3-mercaptopropion ester and treating 3-mercatpopropion ester with amine in the form of gaseous atmosphere as the following reaction 2.

[Reaction 2]

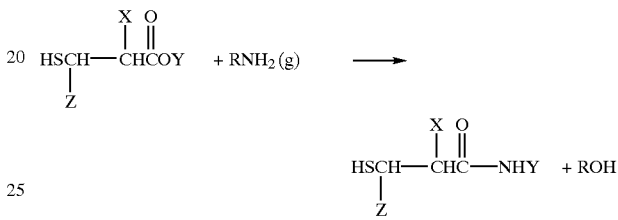

wherein X, Y, Z and R are as defined above.

The method can produce N-substituted-3-mercaptopropionamide with high yield and the reaction may be performed for a short time. i.e. less than 24 hours. However, the produced N-substituted-3-mercaptopropionamide has low purity. Furthermore, as the method uses amine in the form of gaseous atmosphere, the safety and environmental problems occur. Furthermore, water is generated during the method, that can substantially lower the yield of the subsequent halogenation reaction.

U.S. Pat. No. 4,868,310 discloses a method of preparing N-substituted-3-mercaptopropionamide. In the method, a mixture of unsaturated nitrile and alcohol, and strong inorganic acid are cofed in an organic solvent to prepare acrylamide and acrylamide is treated with a thiolating agent. However, water is generated during the method and therefore, the drying step is necessary.

SUMMARY OF THE INVENTION

It is an object of the present invention to provide a method of preparing N,N'-disubstituted-3,3'-dithiodipropionamide having stable property with high yield within a short reaction time.

It is another object to provide the method of preparing N,N'-substituted-3,3'-dithiopriopionamide which can be easily controlled and has safety and environment advantages.

It is another object to provide a method of preparing substituted 3-isothiazolone without generation of water.

It is another object to provide the method of preparing substituted 3-isothiazolone with high yield.

These and other objects may be achieved by a method of preparing N,N-disubstituted-3,3'-dithiodipropionamide of formula 2 comprising the steps of first-reacting 3-mercaptopropionamide of formula 4 with an aqueous solution of amine to prepare N-substituted-3-mercaptopropionamide of formula 3; and second-reacting N-substituted-3-mercaptopropionamide with an aqueous solution of hydrogen peroxide.

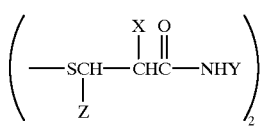
[Formula 2]

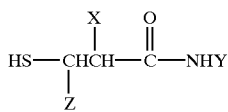
[Formula 3]

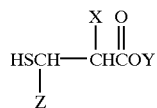
[Formula 4]

wherein X and Z are same or different and each selected from the group consisting of hydrogen or a lower alkyl group;

Y is selected from the group consisting of hydrogen, an alkyl group of 1 to 18 carbon atoms, a cycloalkyl group of up to 10 carbon atoms, an aralkyl group of up to 10 carbon atoms, an aryl group of up to 10 carbon atoms, a halogen-, lower alkyl- or lower alkoxy-substituted aryl group, a cyano alkyl group, a carboalkoxyalkyl group, a haloalkyl group, an alkoxyalkyl group, an aryloxyalkyl group of up to 12 carbon atoms, an aralkoxyalkyl group of up to 12 carbon atoms, a dialkylaminoalkyl group, an alkylacyl group of up to 8 carbon atoms, a lower alkylsulfonyl group, an arylsulfonyl group of up to 10 carbon atoms, a cyano group and a carbamoyl group.

In order to achieve these objects and others, the present invention provides a method of preparing substituted 3-isothiazolone comprising the steps of reacting 3-mercaptopropion ester of formula 4 with an aqueous solution of amine to prepare N-substituted-3-mercaptopropionamide of formula 3; reacting N-substituted-3-mercaptopropionamide with an aqueous solution of hydrogen peroxide to prepare N,N-disubstituted-3,3'-dithiodipropionamide; and reacting N,N-disubstituted-3,3'-dithiodipropionamide with a halogenating agent.

The present invention further includes a method of preparing 5-chloro-2-methyl-3-isothiazolone comprising the steps of reacting 3-mercaptopropion ester with an aqueous solution of methyl amine to prepare N-methyl-3-mercaptopropionamide; reacting N-methyl-3-mercaptopropionamide with an aqueous solution of hydrogen peroixde to prepare N,N'-dimethyl-3,3'-dithiodipropionamide; and reacting N,N'-dimethyl-3,3'-dithiodipropionamide with a halogenating agent selected from the group consisting of chlorine, sulfuryl chloride and N-chlorosuccinimide.

DETAILED DESCRIPTION OF THE INVENTION

The present invention provides a method of preparing N,N'-3,3'-disubstituted-3,3'-dithiodipropionamide.

In the method, 3-mercaptopropion ester of formula 4 reacts with an aqueous solution of amine to form N-substituted-3-mercaptopropionamide. N-substituted-3-mercaptopropionamide reacts with an aqueous solution of hydrogen peroxide.

The present invention further provides a method of preparing substituted 3-isothiazolone by using N,N'-disubstituted-3,3'-dithiodipropionamide as the intermediate.

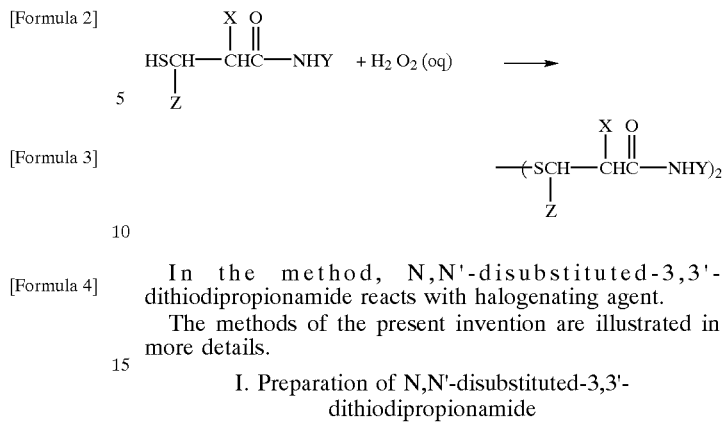

In the method, N,N'-disubstituted-3,3'-dithiodipropionamide reacts with halogenating agent.

The methods of the present invention are illustrated in more details.

I. Preparation of N,N'-disubstituted-3,3'-dithiodipropionamide

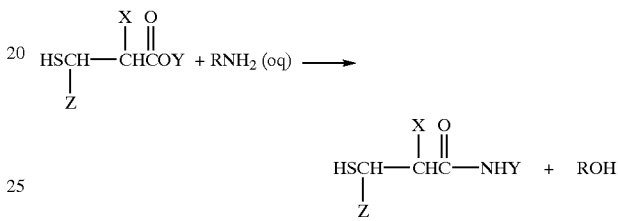

wherein X, Y, Z and R are as defined above.

An aqueous solution of amine is added to 3-mercaptopropion ester and the mixture is shaken for more than 2 hours, preferably, 2 to 40 hours to react. At this time, N-substituted-3-mercaptopropionamide is obtained.

1.0 to 1.5 equivalents of the aqueous solution of amine is preferably added per 1 equivalent of 3-mercaptopropion ester. The amount of amine aqueous solution is less than 1.0 equivalent, yield of N-substituted-3-mercaptopropionamide is reduced. On the contrary, if the amount thereof exceeds 1.5 equivalents, the amount of the unreacted amines increases. The concentration of the aqueous solution of amine is less than 5%, the amounts of reactants increase and reaction efficiency decreases.

In the step, as amine is used in the form of an aqueous solution rather than the gas, it is easily control reaction condition and the method has safety and environment advantages.

Thereafter, the temperature is elevated, thereby to remove the produced alcohol and an organic solvent is added to the resulting product. The organic solvent may be toluene, 1-butanol, methylene chloride, chloroform, hexane, cyclohexane, benzene or the mixture thereof. If the organic solvent is not used, it may be difficult to shake.

At least 10%, more preferably, 35 to 50% an aqueous solution of hydrogen peroxide is added to N-substituted-3-mercaptopropionamide and reacted for more than 0.5 hours, preferably, 0.5 to 20 hours under up to room temperature. 0.4 to 5.5 equivalent of the aqueous solution of hydrogen peroxide is preferably added per 1 equivalent of N-substituted-3-mercaptopropionamide.

The concentration of hydrogen peroxide aqueous solution is less than 10%, the amount of the reactant increases and the reaction efficiency decreases.

In the step, as the hydrogen peroxide is used in the form of the aqueous solution, it is to also easily control the reaction condition. Furthermore, the method has safety and environments advantages.

II. Preparation of Substituted 3-isothiazolone

The produced N,N'-disubstituted-3,3'-dithiodipropionamide reacts with a halogenating agent to form substituted 3-isothiazolone. At this time, drying of N,N'-disubstituted-3,3'-dithiodipropionamide is not necessary, because water is not generated in the preparation of N,N'-disubstituted-3,3'-dithiodipropionamide.

The halogenating agent may be chlorine ($Cl_2$), bromine, sulfuryl chloride ($SOCl_2$), sulfuryl bromide, N-chlorosuccinimide or N-bromosuccinimide.

In the reaction 3, if X and Z are hydrogen, and Y is a methyl group, the method of substituted 3-isothiazolone is as follows:

3-mercaptomethylpropione ester reacts with an aqueous solution of methyl amine to prepare N-methyl-3-mercaptopropionamide. N-methyl-3-mercaptopriopionamide reacts with an aqueous solution of hydrogen peroxide to prepare N,N'-dimethyl-3,3'-dithiodipropionamide. Thereafter, N,N'-dimethyl-3,3'-dithiodipropionamide reacts with a halogenating agent. The halogenating agent may be chlorine, sulfuryl chloride and N-chlorosuccinimide. 5-chloro-2-methyl-3-isothiazolone is obtained.

The present invention will be now explained in more detail by reference to examples which are not limited to the present invention.

I. Preparation of Intermediate for Producing Substituted 3-isothiazolone

1. Preparation of N,N'-methyl-3,3'-dithiodipropionamide

EXAMPLE 1

100 g of an aqueous solution of methyl amine having a concentration of 40% was added to 120 g of 3-mercaptomethylpropion ester under the room temperature and shaken for 17 hours to react. N-methyl-3-mercaptopropionamide was obtained. The temperature was elevated, thereby to remove the produced methanol and 200 g of toluene was added to the resulting product. 25 g of an aqueous solution of hydrogen peroxide having a concentration of 35% was slowly added to the mixture under the room temperature and reacted for 0.5 hours. The filtrating step and drying step were performed. N,N'-dimethyl-3,3'-dithiodipropionamide was obtained.

EXAMPLE 2

N,N'-dimethyl-3,3'-dithiodipropionamide was prepared by the same procedure in Example 1 except that 200 g of methylene chloride was used instead of toluene.

EXAMPLE 3

N,N'-dimethyl-3,3'-dithiodipropionamide was prepared by the same procedure in Example 1 except that 200 g of cyclehexane was used instead of toluene.

EXAMPLE 4

N,N'-dimethyl-3,3'-dithiodipropionamide was prepared by the same procedure in Example 1 except that 200 g of 1-butanol was used instead of toluene.

Comparative Example 1

40 g of methyl amine in the form of gaseous atmosphere was injected into 119 g of N,N'-dimethyl-3,3'-dithiodipropion ester under the room temperature for two hours. At this time, pressure was elevated to 4 atm. After shaking for 40 hours, temperature increased to 65° C., thereby to remove methanol and excess methyl amine. N,N'-dimethyl-3,3'-dithiodipropionamide was obtained.

2. Preparation of N-methyl-3-mercaptopropionamide

Comparative Example 2

40 g of methyl amine in the from of gaseous atmosphere was injected into 120 g of 3-mercaptomethypropion ester under the room temperature for 2 hours. At this time, pressure was elevated to 4 atm. After shaking 17 hours, temperature was elevated to 65° C., thereby to remove methanol and excess methyl amine. N-methyl-3-mercaptopropionamide was obtained.

The yield, purity, reaction time, reaction pressure and water content of products of examples 1–4 and comparative examples 1–2 were determined and the results are shown in Table 1.

TABLE 1

| | Yield [%] | Purity [%] | Reaction time [hour] | Reaction pressure [atm] | Water content [%] |
|---|---|---|---|---|---|
| Example 1 | 92 | 99 | 17 | 0 | — |
| Example 2 | 91 | 98 | 17 | 0 | — |
| Example 3 | 91 | 95 | 17 | 0 | — |
| Example 4 | 91 | 98 | 17 | 0 | — |
| Comparative example 1 | 80 | 80 | 40 | 4 | — |
| Comparative example 2 | 95 | 93 | 17 | 4 | 2.5 |

As shown in Table 1, examples 1–4 can produce desired products with high yield and purity within a short reaction time. Furthermore, as reaction pressures are low in examples 1–4, it is easy to control reaction conditions. Particularly, water is not generated in examples 1–4 that can substantially lower the yield of the subsequent halogenation reaction for producing substituted 3-isothiazolone.

In the comparative example 1, low reaction speed due to physical property of N,N'-disubstituted-3,3'-dithiodipropion ester caused extension of the amide reaction time and decreases of yield. Furthermore, as gaseous atmosphere including amine causes increase of pressure, it is require further equipment for controlling pressure and it is difficult to control the reaction condition.

The comparative example 2 has the problems caused by gaseous amine as well as "—SH" group in molecular. When a compound including "—SH" group was contacted with air, the compound including "—SH" group oxides, thereby to form water. The formed water decreases yield of the halogenation is yield.

II. Preparation of 5-chloro-2-methyl-3-isothiazolone

EXAMPLE 5

200 g of ethanol was added to 28.9 g of N,N'-dimethyl-3,3+-dithiodipropionamide obtained in example 1 and 70 g of sulfuryl chloride ($SO_2Cl_2$) was added to the mixture. 5-chloro-2-methyl-3-isothiazolone was obtained.

EXAMPLES 6–8

5-chloro-2-methyl-3-isothiazolone were prepared by the same procedure in Example 5 except that N,N'-dimethyl-3,3'-dithiodipropionamide obtained in Examples 2–4 were used, respectively.

Comparative Example 3

5-chloro-2-methyl-3-isothiazolone was prepared by the same procedure in Example 5 except that N,N'-dimethyl-3,3'-dithiodipropionamide obtained in comparative example was used.

Comparative Example 4

5-chloro-2-methyl-3-isothiazolone was prepared by the same proceudre in Example 5 except that N-methyl-3-mercaptopropionamide was used.

The yields of products obtained in examples 5–8 and comparative examples 3–4 were determined and the results are shown in Table 2.

TABLE 2

|  | Yield [%] |
|---|---|
| Example 5 | 85 |
| Example 6 | 85 |
| Example 7 | 84 |
| Example 8 | 85 |
| Comparative example 3 | 78 |
| Comparative example 4 | 65 |

As shown in Table 2, examples 5–8 can produce 5-chloro-2-methy-3-isothiazolone, substituted 3-isothiazolone, with high yield.

The method of the present invention can produce stable N,N'-disubstituted-3,3'-dithiodipropionamide with high yield and reduce the reaction time. Furthermore, it is easy to control the reaction condition, the method has safety and environment advantages. As water is not generated during the method, drying step of N,N'-disubstituted-3,3'-dithiopropionamide is not necessary before the halogen reaction and produce 3-isothiazolone with high yield.

While the present invention has been described in detail with reference to the preferred embodiments, those skilled in the art will appreciate that various modifications and substitutions can be made thereto without departing from the spirit and scope of the present invention as set forth in the appended claims.

What is claimed is:

1. A method of preparing substituted 3-isothiazolone comprising the steps of:
   reacting 3-mercaptopropion ester of formula 4 with an aqueous solution of amine to prepare N-substituted-3-mercaptopropionamide of formula 3;
   reacting N-substituted-3-mercaptopropionamide with an aqueous solution of hydrogen peroxide to prepare N,N-disubstituted-3,3'-dithiodipropionamide; and
   reacting N,N-disubstituted-3,3'-dithiodipropionamide with a halogenating agent,

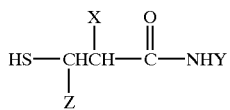
[Formula 3]

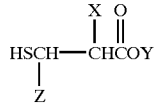
[Formula 4]

wherein X and Z are same or different and each selected from the group consisting of hydrogen or a lower alkyl group;

Y is selected from the group consisting of hydrogen, an alkyl group of 1 to 18 carbon atoms, a cycloalkyl group of up to 10 carbon atoms, an aralkyl group of up to 10 carbon atoms, an aryl group of up to 10 carbon atoms, a halogen-, lower alkyl- or lower alkoxy-substituted aryl group, a cyano alkyl group, a carboalkoxyalkyl group, a haloalkyl group, an alkoxyalkyl group, an aryloxyalkyl group of up to 12 carbon atoms, an aralkoxyalkyl group of up to 12 carbon atoms, a dialkylaminoalkyl group, an alkylacyl group of up to 8 carbon atoms, a lower alkylsulfonyl group, an arylsulfonyl group of up to 10 carbon atoms, a cyano group and a carbamoyl group.

2. The method of claim 1, wherein the halogenating agent is selected from the group consisting of chlorine, bromine, sulfuryl chloride, sulfuryl bromide, N-chlorosuccinimide and N-bromosuccinimide.

3. A method of preapring 5-chloro-2-methyl-3-isothiazolone comprising the steps of:
   reacting 3-mercaptopropion ester with an aqueous solution of methyl amine to prepare N-methyl-3-mercaptopropionamide;
   reacting N-methyl-3-mercaptopropionamide with an aqueous solution of hydrogen peroixde to prepare N,N'-dimethyl-3,3'-dithiodipropionamide; and
   reacting N,N'-dimethyl-3,3'-dithiodipropionamide with a halogenating agent, the halogenating agent being selected from the group consisting of chlorine, sulfuryl chloride and N-chlorosuccinimide.

* * * * *